US009162287B2

(12) United States Patent
Ujihara et al.

(10) Patent No.: US 9,162,287 B2
(45) Date of Patent: Oct. 20, 2015

(54) BIOCOMPATIBLE CONFEITO-LIKE GOLD NANOPARTICLES, METHOD FOR MAKING THE SAME, AND THEIR BIOMEDICAL APPLICATIONS

(75) Inventors: Masaki Ujihara, Taipei (TW); Toyoko Imae, Taipei (TW)

(73) Assignee: NATIONAL TAIWAN UNIVERSITY OF SCIENCE AND TECHNOLOGY, Taipei (TW)

(*) Notice: Subject to any disclaimer, the term of this patent is extended or adjusted under 35 U.S.C. 154(b) by 131 days.

(21) Appl. No.: 13/333,868

(22) Filed: Dec. 21, 2011

(65) Prior Publication Data

US 2013/0164842 A1 Jun. 27, 2013

(51) Int. Cl.
| | |
|---|---|
| B22F 9/24 | (2006.01) |
| C12N 5/10 | (2006.01) |
| C22C 5/02 | (2006.01) |
| A61K 41/00 | (2006.01) |
| B22F 1/00 | (2006.01) |
| B82Y 30/00 | (2011.01) |
| B82Y 5/00 | (2011.01) |

(52) U.S. Cl.
CPC ............... *B22F 9/24* (2013.01); *A61K 41/0052* (2013.01); *B22F 1/0018* (2013.01); *B82Y 30/00* (2013.01); *C12N 5/10* (2013.01); *C22C 5/02* (2013.01); *B22F 1/0062* (2013.01); *B22F 2001/0033* (2013.01); *B82Y 5/00* (2013.01); *Y10T 428/12014* (2013.01)

(58) Field of Classification Search
CPC .................. B01J 13/00–13/0043; B22F 9/00; B22F 9/16; B22F 9/18; B22F 2009/24; B22F 1/0044; B22F 1/0007; B22F 1/0018; B22F 1/0022; B22F 1/0062; A61K 49/0065
See application file for complete search history.

(56) References Cited

PUBLICATIONS

Biswa Ranjan Panda and Arun Chattopadhyay, Synthesis of Au Nanoparticles at "all" pH by H2O2 Reduction of HAuCl4, 2007, Journal of Nanoscience and Nanotechnology, vol. 7, pp. 1911-1915.*
Jong-Hee Lee, Kai Kamada, Naoya Enomoto, Junichi Hojo, Morphology-selective synthesis of polyhedral gold nanoparticles: What factors control the size and morphology of gold nanoparticles in a wet-chemical process, 2007, Journal of Colloid and Interface Science, vol. 316, pp. 887-892.*
Francesca Porta, Laura Prati, Michele Rossi, and Giorgio Scarff, New Au(0) Sols as Precursors for Heterogeneous Liquid-Phase Oxidation Catalysts, 2002, Journal of Catalysis 211, 464-469.*
Toshio Sakai and Paschalis Alexandridis, Mechanism of Gold Metal Ion Reduction, Nanoparticle Growth and Size Control in Aqueous Amphiphilic Block Copolymer Solutions at Ambient Conditions, 2005, J. Phys. Chem. B, 109, 7766-7777.*
Wolfgang Weinert, Oral Hygiene Products, 2000, Ulmann's Encyclopedia of Industrial Chemisty vol. 25, pp. 499-505.*
Mari Yamamoto, Yukiyasu Kashiwagi, Takao Sakata, Hirotaro Mori, and Masami Nakamoto, Synthesis and Morphology of Star-Shaped Gold Nanoplates Protected by Poly(N-vinyl-2-pyrrolidone), 2005, Chem. Mater., vol. 17, No. 22, pp. 5391-5393.*
Yen Hsun Su, Wei Hao Lai, Wei-Yu Chen, Min Hsiung Hon, and Shih-Hui Chang, Surface plasmon resonance of gold nano-sea-urchin, 2007, Appl. Phys. Lett. 90, 181905.*

\* cited by examiner

*Primary Examiner* — Ralph Gitomer
*Assistant Examiner* — Trent Clarke
(74) *Attorney, Agent, or Firm* — WPAT, P.C.; Anthony King

(57) ABSTRACT

The present invention provides a method for producing gold nanoparticles using hydroxyl peroxide in an aqueous alkaline condition in the presence of a biocompatible protecting agent. The method of the invention does not involve toxic reagents and therefore are environmentally friendly. The gold nanoparticles thus produced can be used in biomedical applications including cancer therapy and drug delivery without purification.

1 Claim, 4 Drawing Sheets

BIOCOMPATIBLE CONFEITO-LIKE GOLD NANOPARTICLES, METHOD FOR MAKING THE SAME, AND THEIR BIOMEDICAL APPLICATIONS

FIELD OF THE INVENTION

The present invention relates to confeito-like gold nanoparticles (C-AuNPs), a method for making the same and their biomedical applications.

BACKGROUND OF THE INVENTION

Biocompatible gold nanoparticles (AuNPs) are preferably used as markers in living tissues. Meanwhile, anisotropic AuNPs have gathered great attention because they have a strong absorption band in the near-infrared (NIR) range in which the light can penetrate deeply into the human body. Moreover, when the anisotropic AuNPs can absorb the near-infrared light, they generate heat enough to kill cancer cells. Whereas gold nano-rods are one group of the typical anisotropic nanoparticles and are investigated as imaging systems and on cancer therapy, there are main issues on practical use of the nano-rods, namely, the messy synthesis process and their toxicity. To synthesize nano-rods, "seed particles" and a concentrated surfactant solution are needed, and the reaction takes long time (at least several hours). The surfactant used is toxic and hard to remove from the obtained gold nano-rods. These issues limit practical usages of the gold nano-rods. The other anisotropic nanoparticles also have similar problems for the multiple procedures and/or the toxicity of protecting agents.

Thus, there is a need for biocompatible gold nanoparticles with NIR absorption, and also a need for a concise process for synthesizing AuNPs.

BRIEF SUMMARY OF THE INVENTION

The present invention is based on the unexpected finding that using hydroxyl peroxide as a reducing agent in an aqueous alkaline condition in the presence of a biocompatible protector, gold nanoparticles with a confeito-like shape can be obtained from a gold precursor with no toxic byproducts. In this invention, the reducing agent i.e. hydroxyl peroxide can be decomposed to water and a biocompatible protector can be selected to accomplish the synthesis of the gold nanoparticles. Accordingly, the AuNPs of the invention do not contain toxic compounds and can be used in medical applications without purification processes. In addition, the synthesis reaction of the invention is accomplished within short time and suitable for mass production.

In one aspect, the present invention provides a method for producing gold nanoparticles, which comprises reducing a gold precursor with hydroxyl peroxide in an aqueous alkaline condition in the presence of a biocompatible protecting agent. In certain embodiments of the invention, the biocompatible protecting agent is selected from the group consisting of citrate, poly(ethylene oxide)-poly(propylene oxide) block copolymer (PEO-PPO block copolymer, e.g. PF-127, a commercially available biocompatible triblock copolymer) and poly(vinyl pyrrolidone).

In another aspect, the invention provides gold nanoparticles produced by the method as described herein, which is biocompatible and non-toxic.

Also provided is a method of cancer therapy, which comprises introducing the gold nanoparticles as described herein to cancer cells and irradiating the cancer cells with radiation for killing the cancer cells. Particularly, the radiation is a near-infrared irradiation at 785 nm.

Further provided is a method of drug delivery, which comprises introducing a drug adsorbed on the gold nanoparticles as described herein to cells and irradiating the cells with radiation for deforming the nanoparticles to spherical nanoparticles to allow a controlled release of the drugs without damages to cells. Particularly, the radiation is a near-infrared irradiation at 633 nm.

The present invention also provides use of the gold nanoparticles as described herein for the manufacture of a composition as a medicament for cancer therapy or a carrier for drug delivery.

It is believed that a person of ordinary knowledge in the art where the present invention belongs can utilize the present invention to its broadest scope based on the descriptions herein with no need of further illustration. Therefore, the following descriptions should be understood as of demonstrative purpose instead of limitative in any way to the scope of the present invention.

BRIEF DESCRIPTION OF THE SEVERAL VIEWS OF THE DRAWINGS

For the purpose of illustrating the invention, there are shown in the drawings embodiments which are presently preferred. It should be understood, however, that the invention is not limited to the preferred embodiments shown.

In the drawings.

DETAILED DESCRIPTION OF THE INVENTION

Figure 1:
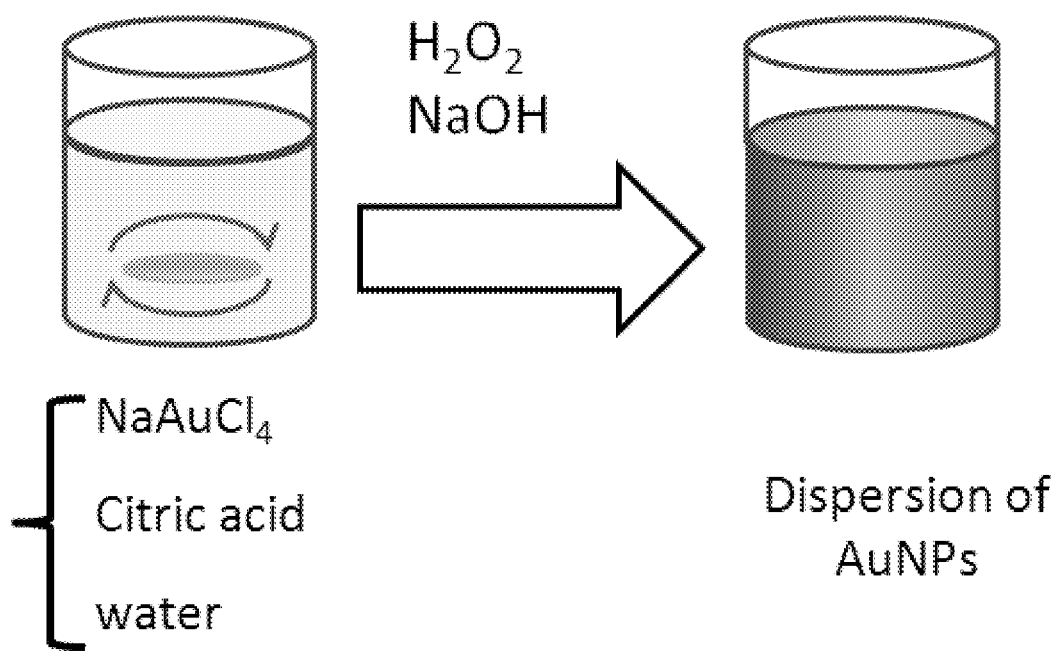
FIG. 1 shows the synthesis scheme of the AuNPs of the invention.

Unless defined otherwise, all technical and scientific terms used herein have the same meaning as commonly understood by a person skilled in the art to which this invention belongs. All publications mentioned herein are incorporated herein by reference to disclose and describe the methods and/or materials in connection with which the publications are cited.

As used herein, the singular forms "a", "an", and "the" include plural referents unless the context clearly dictates otherwise. Thus, for example, reference to "a sample" includes a plurality of such samples and equivalents thereof known to those skilled in the art.

In one aspect, the present invention provides a method for producing gold nanoparticles, which comprises reducing a gold precursor with hydroxyl peroxide in an aqueous alkaline condition in the presence of a biocompatible protecting agent.

As used herein, a gold precursor refers to a precursor material that comprises gold in an oxidation state greater than zero (e.g., $Au^+$, $Au^{+3}$) and is capable of being reduced to form gold atoms. Particularly, a gold salt, including but not limited to, $NaAuCl_4$, $AuCl_3$, $NaAuBr_4$, and $KAuCl_4$, and hydrates and solvates thereof, may be used as a gold precursor in the present invention. In certain examples, a gold precursor is dissolved in water, forming an aqueous gold precursor solution for the subsequent procedure.

As used herein, a protecting agent is a substance or a compound that can control and stabilize the particle size distribution of metal nanoparticles. Particularly, a protecting agent can be chemically or physically bonded to the metal nanoparticles and thus to prevent aggregation of the metal nanoparticles and to control and stabilize the particle size distribution of the metal nanoparticles to a proper range. By adding a protective agent, the condition wherein the metal nanoparticles having a small particle size is suspended is maintained. Various protecting agents for synthesis of gold nanoparticles are known and available in the art. According to the invention, the protecting agent is biocompatible.

The term "biocompatible" means that the protecting agent does not cause severe toxicity or adverse biological reaction in an animal when administered at a reasonable dose. Typically, a biocompatible protecting agent is biological inert and non-toxic to living cells or tissues; for example, its addition to cells results in less than 30% cell death, preferably less than 20% cell death, more preferably less than 10% cell death. Suitable examples of biocompatible protecting agents as used in the present invention include but are not limited to citrate, poly(ethylene oxide)-poly(propylene oxide) block copolymer and poly(vinyl pyrrolidone). In certain examples, after a gold precursor is dissolved in water, forming an aqueous gold precursor solution, a biocompatible protecting agent is added to the aqueous gold precursor solution, forming a reaction mixture for the subsequent procedure. Specifically, the gold precursor is added in an amount to have a concentration from 0.01 to 5 mM, preferably from 0.01 to 1 mM, and more preferably from 0.05 to 0.5 mM, and the biocompatible protecting agent is added in an amount to have a concentration from 0.005 to 1 wt %, preferably from 0.01 to 0.5 wt %, and more preferably from 0.01 to 0.2 wt %, in the reaction mixture.

According to the invention, hydroxy peroxide is used as a reducing agent to reduce a gold precursor to produce the gold nanoparticles of the invention. In certain examples, after a biocompatible protecting agent is added to an aqueous gold precursor solution, forming a reaction mixture, hydroxy peroxide is then added to the reaction mixture. In certain examples, hydroxyl peroxide is added to have a concentration from 1 to 200 mM, preferably from 10 to 100 mM, and more preferably from 10 to 50 mM, in the reaction mixture.

According to the invention, reduction of a gold precursor using hydroxy peroxide to produce the gold nanoparticles of the invention is performed in an aqueous alkaline condition. Particularly, the pH of the aqueous alkaline condition is about 10 or greater, more particularly between 10 and 13, and even more particularly between 10 and 12. In certain examples, after hydroxyl peroxide is added to the reaction mixture, the pH of the reaction mixture is then adjusted by adding a base to the reaction mixture. The base may be any suitable based e.g. NaOH and may be added at an appropriate amount to adjust the pH as desired as above. In one example, the base may be added at once to the reaction mixture with vigorous stirring.

Following adjustment of the pH of the reaction mixture, the reaction mixture may be maintained at a suitable temperature for a period of time sufficient to form dispersions of the gold nanoparticles of the invention. In some embodiments, the reaction mixture may be maintained at ambient temperature or above or below the same, for example between about 0° C. and about 60° C., between about 10° C. and about 40° C., or between about 15° C. and about 35° C. In some embodiments, the reaction mixture may be maintained at a suitable temperature for between about 0.5 hr, about 1 hr, about 2 hrs, about 4 hrs, or more.

In one certain embodiment, the method of the invention is conducted by (i) dissolving a gold salt in water to prepare an aqueous gold precursor solution, (ii) dissolving a biocompatible protecting agent (e.g. citrate, PEO-PPO block copolymer or poly(vinyl pyrrolidone) in the gold precursor solution to produce a reaction mixture, (iii) adding hydroxyl peroxide to the reaction mixture, (iv) subsequently adding an aqueous solution of a base to adjust the pH of the resulting reaction mixture to pH 10 or more, and (iv) placing the resulting reaction mixture at about 25° C. for about 1 hr. Working examples of the method of the invention are provided below.

In another aspect, the present invention provides gold nanoparticles produced by the method as described herein.

According to the invention, the gold nanoparticles thus produced are non-toxic and biocompatible, which can be used for medical applications without purification.

Specifically, by means of analysis by transmission electron microscopy (TEM), scanning electron microscopy (SEM), the gold nanoparticles of the invention are found to have a confeito-liked shape. More specifically, the gold nanoparticles of the invention have a mean particle size of from 20 to 500 nm and even more specifically from 50 to 300 nm, in diameter. These nanoparticles are uniform in shape and size, having smaller sized protuberances (diameter around 30 nm, length around 40 nm) in large numbers protruding from the body. Even more specifically, the gold nanoparticles of the invention have a broad absorption band extending to the near-infrared region, particularly from 300 to 1200 nm and more particularly exhibit a relatively strong absorption band from 450 to 800 nm.

One of the features of the AuNPs of the invention is having a strong absorption band in the near-infrared range. Thus, they can be used as an imaging reagent and a killer of cancer cells on the biomedical applications. Moreover, the confeito-like structures are thermally unstable and can be changed to spherical ones by a strong near-infrared wave irradiation. This deformation of confeito-like structure allows a controlled-release of drugs which are adsorbed on AuNPs of the invention. These characteristics indicate that AuNPs of the invention are superior on the imaging and therapy as well as nano-rods, although the latter particles have issues on the biomedical applications.

More specifically, cancer cells (e.g. HeLa cells) can be killed by a short-time irradiation of a near-infrared laser (e.g. at wavelength of 785 nm) when the AuNPs of the invention exists in the cells. This carcinolysis is likely due to the strong plasmon absorption of the AuNPs at the near-infrared region. On the other hand, the cancer cells including the AuNPs can survive for the irradiation at the wavelength of 633 nm, which is near the plasmon absorption band of the AuNPs. In this condition, the AuNPs are quickly converted to small spherical nanoparticles, and the resulted small nanoparticles are less photoactive than the AuNPs. This conversion suggests that the AuNPs of the invention are useful for the controlled drug-releasing devises.

Accordingly, in one embodiment, the present invention provides a method of cancer therapy, which comprises introducing the gold nanoparticles as described herein to cancer cells and irradiating the cancer cells with radiation for killing the cancer cells. Specifically, the radiation is a near-infrared irradiation at 785 nm.

In another embodiment, the present invention provides a method of drug delivery, which comprises introducing a drug adsorbed on the gold nanoparticles as described herein to cells and irradiating the cells with radiation for deforming the nanoparticles to spherical nanoparticles to allow a controlled release of the drugs without damages to cells. Specifically, the radiation is an irradiation at 633 nm.

The present invention is further illustrated by the following examples, which are provided for the purpose of demonstration rather than limitation.

Example 1

Synthesis of the Gold Nanoparticles of the Invention 1.1 Materials and Methods

Sodium tetrachloroaurate(III) dihydrate ($NaAuCl_4 \cdot 2H_2O$) and Pluronic F-127 (a polyethylene oxide-polypropylene oxide-polyethylene oxide block copolymer, PF127) were purchased from Sigma Aldrich Co. (USA). Anhydrous citric acid (Cit), polyvinylpyrrolidone (PVP, average M.W.: 58,000), sodium hydroxide (NaOH), and an aqueous 35 wt % solution of hydrogen peroxide ($H_2O_2$) were purchased from Acros Organics (USA). All chemicals were of reagent grade and were used without further purification. Ultrapure (Millipore Milli-Q) water with a resistivity of 18 MΩ·cm was used throughout all the syntheses and measurements in the study.

The synthesis of AuNPs was performed in a 50 $cm^3$ glass vial at ambient temperature. Specifically, 4 $cm^3$ of an aqueous 1 mM solution of $NaAuCl_4$ was diluted with 28 $cm^3$ of water, and a specified amount of the protecting agent was dissolved in the solution. An aqueous solution of $H_2O_2$ (80 $mm^3$) was added to the solution, and an aqueous 100 mM solution of NaOH (8 $cm^3$) was then added with vigorous stirring. After 5 min, the stirring was slowed down and continued for 1 h. The reaction solution was allowed to stand overnight for the reaction to go to completion, and a dispersion of AuNPs was obtained.

1.2 Using Citric Acid as a Protecting Agent

The AuNPs of the invention were synthesized in a one-pot process. First, an aqueous solution of $NaAuCl_4$ (1 mM, 4 $cm^3$) was diluted with 28 $cm^3$ of water, and a specified amount (16.0 mg) of citric acid (a protecting agent) was dissolved in the solution. The concentration of the gold salt and that of the protecting agent in the solution were about 0.125 mM and 0.05 wt %, respectively. An aqueous solution of $H_2O_2$ (35 wt %, 80 $mm^3$) was added into the solution (the concentration of $H_2O_2$ was about 29 mM in the solution), and an aqueous solution of NaOH (100 mM, 8 $cm^3$) was poured there at once with vigorous stirring to adjust the pH of the solution to be about pH 10.6. After 5 min, the stirring was slowed down and kept for 1 hour at 25° C. Finally, dispersions of AuNPs were obtained accordingly. FIG. 1 illustrates the synthesis scheme of the AuNPs of the invention.

1.3 Using Poly(Ethylene Oxide)-Poly(Propylene Oxide) Block Copolymer as a Protecting Agent The AuNPs of the invention were synthesized in a one-pot process. First, an aqueous solution of $NaAuCl_4$ (1 mM, 4 $cm^3$) was diluted with 28 $cm^3$ of water, and a specified amount (40.0 mg) of poly(ethylene oxide)-poly(propylene oxide) block copolymer (a protecting agent) was dissolved in the solution. The concentration of the gold salt and that of the protecting agent in the solution were about 0.125 mM and about 0.125 wt %, respectively. An aqueous solution of $H_2O_2$ (35 wt %, 80 $mm^3$) was added into the solution (the concentration of $H_2O_2$ was about 29 mM in the solution), and an aqueous solution of NaOH (100 mM, 8 $cm^3$) was poured there at once with vigorous stirring to adjust the pH of the solution to be about pH 11.4. After 5 min, the stirring was slowed down and kept for 1 hour at 25° C. Finally, dispersions of AuNPs were obtained accordingly. FIG. 1 illustrates the synthesis scheme of the AuNPs of the invention.

1.4 Using Poly(Vinyl Pyrrolidone) as a Protecting Agent

The AuNPs of the invention were synthesized in a one-pot process. First, an aqueous solution of $NaAuCl_4$ (1 mM, 4 $cm^3$) was diluted with 28 $cm^3$ of water, and a specified amount (40.0 mg) of poly(vinyl pyrrolidone) (a protecting agent) was dissolved in the solution. The concentration of the gold salt and that of the protecting agent in the solution were about 0.125 mM and about 0.125 wt %, respectively. An aqueous solution of $H_2O_2$ (35 wt %, 80 $mm^3$) was added into the solution (the concentration of $H_2O_2$ was about 29 mM in the solution), and an aqueous solution of NaOH (100 mM, 8 $cm^3$) was poured there at once with vigorous stirring to adjust the pH of the solution to be about pH 11.6. After 5 min, the stirring was slowed down and kept for 1 hour at 25° C. Finally, dispersions of AuNPs were obtained accordingly. FIG. 1 illustrates the synthesis scheme of the AuNPs of the invention.

Example 2

Characterization of the Gold Nanoparticles of the Invention 2.1 Instruments

Transmission electron microscopy (TEM) images were acquired with a Hitachi H-7000 instrument at an accelerating voltage of 100 kV. The dispersion of AuNPs was poured on a carbon-coated copper grid, air-dried, and then used for the observation. The scanning electron microscopy (SEM) images were obtained with a JEOL JSM-6500F microscope. Ultraviolet-visible-near infrared (UV-vis-NIR) absorption spectra were recorded with a JASCO V-670 spectrophotometer with a quartz cell with a 1 cm light path.

2.2 Results

The AuNPs obtained in Example 1 were analyzed by visual observation and adequate apparatuses, including transmission electron microscopy (TEM), scanning electron microscopy (SEM), and UV-Vis-NIR absorption spectrometer.

Figure 2:
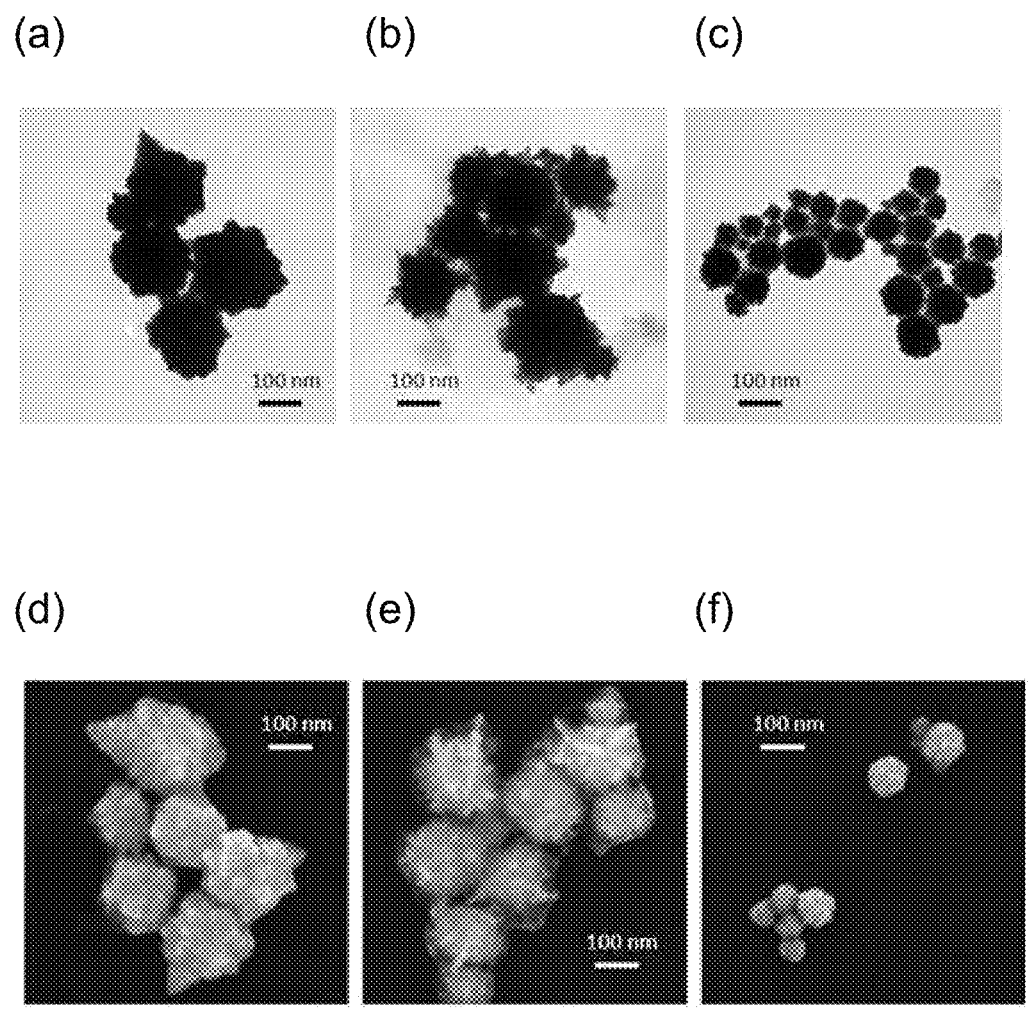
FIG. 2 shows the images of the AuNPs of the invention synthesized with different protecting agents, (a) and (d) citric acid, (b) and (e) PF-127, and (c) and (f) poly(vinyl pyrrolidone), by transmission electron microscopic (upper column; (a), (b) and (c)) and scanning electron microscopic (lower column; (d), (e) and (f)).
Figure 3:
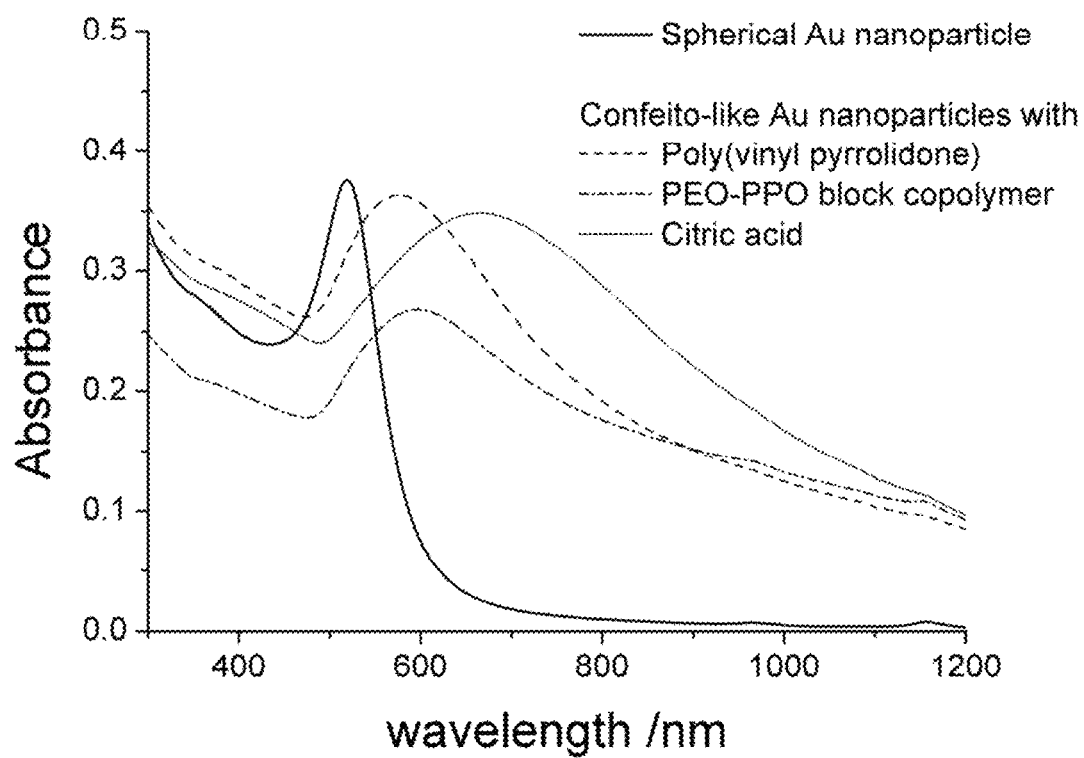
FIG. 3 shows the UV-Vis-NIR absorption spectra of the AuNPs of the invention synthesized with different protecting agents, poly(vinyl pyrrolidone), PEO-PPO block copolymer, and citric acid (various dashed lines); and the spectraum of traditional spherical Au nanoparticles (solid line).

It is known that the color of a gold nanoparticle solution depends on the size and shape of the nanoparticles. Individual small gold nanoparticles appear red while the color changes from red to blue when the particles aggregate. In the visual observation (data not shown), it was shown that the AuNPs of the invention, synthesized by using citric acid, poly(ethylene oxide)-poly(propylene oxide) block copolymer, or poly(vinyl pyrrolidone), as a protecting agent, as in Example 1, were ranging from blue-violet to dark blue. In the TEM and SEM analyses (FIG. 2), it was shown that the AuNPs of the invention had a mean particle size of from 20 to 500 nm, more specifically from 50 to 300 nm and were in confeito-like shapes, having smaller sized protuberances (about 30 nm in diameter and 40 nm in length) in large numbers protruding from the body. In the spectrum analysis (FIG. 3), it was shown that the AuNPs of the invention exhibited absorption not only in visible light range but also in near-infrared (NIR), specifically ranging from 300 to 1200 nm, and more specifically a relatively strong absorption in the range from 450 to 800 nm, while the spherical AuNPs (control) exhibited absorption only in visible light range (no absorption in NIR range).

Example 3

Biomedical Applications 3.1 Instruments

Optical microscopic observation was performed using a confocal scanning laser microscope (Leica TCS SP5), and laser irradiations were carried out at 785 nm (1.07 W), 633 nm (10 mW), and 561 nm (10 mW) using the microscope system.

3.2 Synthesis and Surface-Modification of AuNPs

The confeito-like AuNPs of the invention were synthesized as in Example 1. To the dispersion of the confeito-like AuNP (40 cm$^3$), an aqueous dispersion of folic acid (2 mM, 0.4 cm$^3$) was added. The mixture was centrifuged at 3000 rpm for 10 min, and then, the fraction of 1 cm$^3$ including the nanoparticles were redispersed to 8 cm$^3$ to adjust the concentration to 0.5 mM (as Au). The spherical AuNPs and plate-like AuNPs for comparison were synthesized as follows:

Spherical AuNPs

An aqueous solution of NaAuCl$_4$ (1 mM, 10 cm$^3$) was boiled with stirring in a glass vial. To this solution, an aqueous solution of trisodium citrate (1 wt %, 1 cm$^3$) was added. Then, the reaction solution was refluxed at 100° C. for 10 minutes with vigorous stirring. After the solution changed the color to red, the solution was stood to cool. To the obtained dispersion of AuNP, an aqueous solution of folic acid (2 mM, 0.025 cm$^3$) was added. Then, the dispersion was diluted to 20 cm$^3$ with water to adjust the concentration to 0.5 mM (as Au).

Plate-Like AuNPs

An aqueous solution of NaAuCl$_4$ (1 mM, 4 cm$^3$) and an aqueous solution of citric acid (1 wt %, 1 cm$^3$) were mixed with 35 cm$^3$ of water, and the reaction solution was allowed to stand overnight at ambient temperature. To the obtained dispersion, an aqueous solution of folic acid (2 mM, 0.4 cm$^3$) was added. Then, the obtained dispersion of AuNP was centrifuged at 3000 rpm for 10 min. Then, the fraction of 1 cm$^3$ including the nanoparticles were redispersed to 8 cm$^3$ to adjust the concentration to 0.5 mM (as Au).

3.3 Uptake of Nanoparticles into Hela Cells and Laser Treatments on the Cells

The dispersion of AuNPs (0.1 cm$^3$) was added to a culture medium of HeLa cell (5×10$^5$ cells), and the cells were incubated for 2 hrs at 37° C. Then, a laser light was irradiated to the cell under a microscope for 20-40 sec.

3.4 Results

The folic acid added in the dispersions is supposed to adsorb on the surface of nanoparticles to facilitate the uptake into the HeLa cell (cervical cancer cell lines). After the incubation time of 2 hrs with AuNPs, the cells were observed by a confocal scanning laser microscope to confirm if they were alive. The cells were not damaged by the AuNPs, and the nanoparticles were recognized inside the cells (data not shown). The individual AuNP of the invention could be observed as bright spots in the dark field image after even long period (few days), and it was confirmed that the cancer cells took the AuNPs of the invention into their bodies without carcinolysis. Thus, the observation verified that the AuNPs of the invention are biocompatible, as estimated from the synthesis procedure. However, the AuNPs-taken cells were killed within several minutes under a laser at wavelength of 785 nm (FIG. 4(a), right). This suggests that AuNPs of the invention absorbed the light and generated heat to kill the cancer cells.

Figure 4:
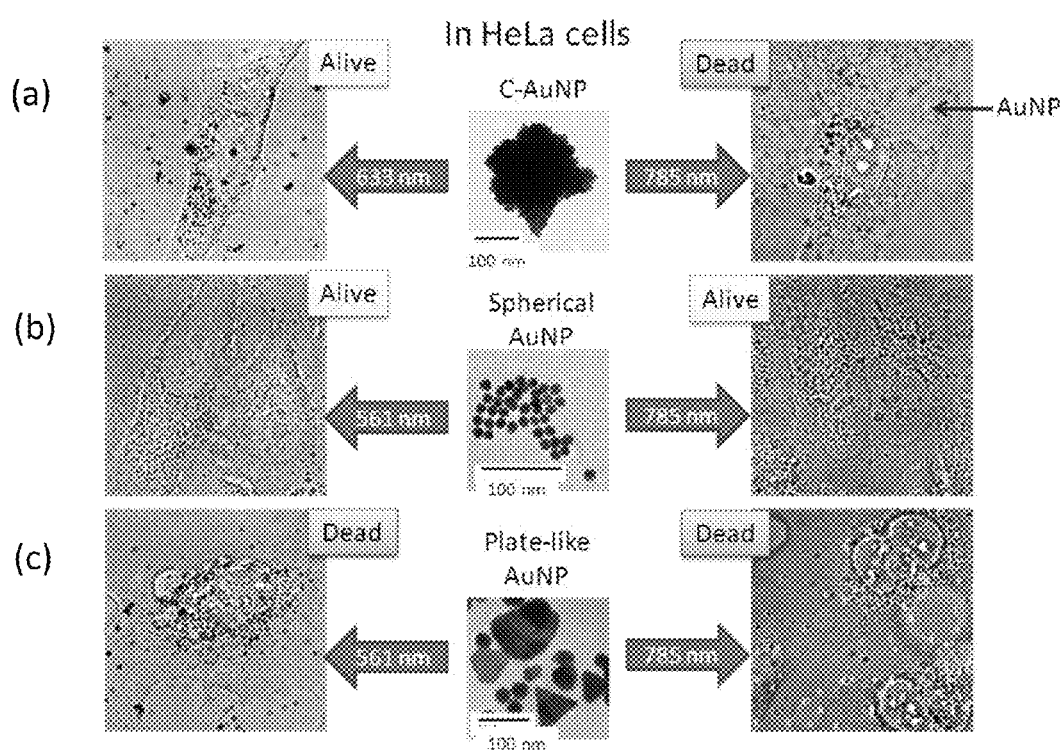
FIG. 4 shows the results of laser irradiation on HeLa cells treated with different gold nanoparticles under a laser at different wavelengths, wherein (a) refers to the cells treated with the C-AuNPs of the invention under a laser at 633 nm (left) and 785 nm (right), (b) refers to the cells treated with spherical AuNPs under a laser at 561 nm (left) and 785 nm (right), and (c) refers to the cells treated with plate-like AuNPs under a laser at 561 nm (left) and 785 nm (right).

On the other hand, the AuNPs-taken cells were not damaged at the irradiation of 633 nm although the wavelength was coincident with its surface plasmon band, but meanwhile the bright spots of AuNPs of the invention became dark (FIG. 4(a), left). This phenomenon implies that the AuNPs of the invention efficiently absorbed the laser light and quickly changed their shapes to the spherical ones. This suggests that the confeito-like AuNPs are also useful as the drug-releasing system which can be controlled by the laser irradiation at this wavelength.

Thus, the AuNPs of the invention under a laser at different wavelength shows different behavior and thus provide different utilization, such as cancer therapy and drug delivery.

For comparison, small spherical gold nanoparticles (diameter: 10 to 20 nm; FIG. 4(b), left and right) and large plate-like gold nanoparticles (diameter: 100 nm~; FIG. 4(c), left and right) were examined with similar procedure and the remarkable differences was observed. While the plate-like and spherical AuNPs absorbed the laser light at 561 nm, only the plate-like AuNP killed the cells under the irradiations at this wavelength. The cells treated with spherical gold nanoparticles under a laser at 561 nm (FIG. 4(b), left) and 785 nm (FIG. 4(b), right) were both alive, and the cells treated with plate-like gold nanoparticles under a laser at 561 nm (FIG. 4(c), left) and 785 nm (FIG. 4(c), right) were both dead.

The present invention will now be described more specifically with reference to the following embodiments, which are provided for the purpose of demonstration rather than limitation.

We claim:

1. A method for producing confeito-like gold nanoparticles, comprising
    (i) preparing an aqueous solution including (a) 0.125 mM NaAuCl$_4$, 0.05 wt % citrate and 0.0875 wt % H$_2$O$_2$; (b) 0.125 mM NaAuCl$_4$, 0.125 wt % poly(ethylene oxide)-poly(propylene oxide) block copolymer being Pluronic F-127 and 0.0875 wt % H$_2$O$_2$; or (c) 0.125 mM NaAuCl$_4$, 0.125 wt % poly(vinyl pyrrolidone) and 0.0875 wt % H$_2$O$_2$;
    (ii) subsequently adding a base to the aqueous solution to adjust the pH to pH 10 or more; and
    (iii) placing the resulting mixture at ambient temperature for a period of time to form the confeito-like gold nanoparticles.

* * * * *